(12) United States Patent
Teng

(10) Patent No.: US 7,071,194 B2
(45) Date of Patent: Jul. 4, 2006

(54) METHOD FOR IMPROVING RESPIRATORY FUNCTION AND INHIBITING MUSCULAR DEGENERATION

(75) Inventor: Yang D. Teng, Wellesley, MA (US)

(73) Assignee: The Children's Medical Center Corporation, Boston, MA (US)

(*) Notice: Subject to any disclaimer, the term of this patent is extended or adjusted under 35 U.S.C. 154(b) by 0 days.

(21) Appl. No.: 10/244,087

(22) Filed: Sep. 13, 2002

(65) Prior Publication Data

US 2003/0139422 A1 Jul. 24, 2003

Related U.S. Application Data

(63) Continuation of application No. PCT/US01/40291, filed on Mar. 14, 2001.

(60) Provisional application No. 60/189,241, filed on Mar. 14, 2000.

(51) Int. Cl.
 A61K 31/497 (2006.01)
 A61K 31/135 (2006.01)
 A61K 33/02 (2006.01)

(52) U.S. Cl. ............... 514/252.15; 514/647; 514/649; 514/657

(58) Field of Classification Search ............. 514/647, 514/252.15, 649, 657
 See application file for complete search history.

(56) References Cited

U.S. PATENT DOCUMENTS

| | | |
|---|---|---|
| 5,530,029 A | 6/1996 | Maltin |
| 5,541,188 A | 7/1996 | Maltin |
| 5,552,442 A | 9/1996 | Maltin |
| 5,885,976 A * | 3/1999 | Sandyk .................. 514/159 |

FOREIGN PATENT DOCUMENTS

WO  WO 01/68073  9/2001

OTHER PUBLICATIONS

Garner et al, 110CA:185838, 1989.*
Lalley et al, 121CA: 1611, 1994.*
Van Der Heijden, 129CA:254758, 1998.*
Merck Manual of Medical Information, Berkow et al Eds, Pocket Books, New York, 1997, pp. 361-362.*
Teng et al. Treatment with 5HT1A receptor agonists reverses respiratory abnormalities spinal cord injured rats, Society for Neuroscience Abstracts, 1999, vol. 25, No. 1-2, p. 1333. Meeting held on Oct. 23-28, 1999.*
Agbenya, E.T., et al., "Effect of Clenbuterol on Normal and Denervated Muscle Growth and Contractility," *Muscle and Nerve*, 13:199-203 (1990).
Bardsley, R.G., et al., "Effect of β-agonists on Expression of Calpain and Calpastatin Activity in Skeletal Muscle, " *Biochmic*, 267-273 (1992).
Brown, R.H., Jr., "Amyotrphic Lateral Schlerosis," *Arch. Neurol.*, 54:1246-1250 (1997).

(Continued)

*Primary Examiner*—Shengjun Wang
(74) *Attorney, Agent, or Firm*—Hamilton, Brook, Smith & Reynolds, P.C.

(57) ABSTRACT

The present invention provides a method for improving respiratory function and inhibiting muscular degeneration (e.g., dystrophy and atrophy). Alternative embodiments of the invention provide a method of inhibiting motor neuron apoptosis and the subsequent muscular degeneration associated with the denervation of muscular tissue resulting from neuron death.

11 Claims, 7 Drawing Sheets

OTHER PUBLICATIONS

Chancellor, A.M., et al., "Adult onset Motor Neuron Disease: Worldwide Mortality, Incidence and Distribution Since 1950," *Journal of Neurology, Neurosurgery and Psychiatry*, 55:1106-1115 (1992).

Culmsee, C., et al., "Clenbuterol Induces Growth Factor mRNA, Activates Astrocytes, and Protects Rat Brain Tissue Against Ischemic Damage," *European Journal of Pharmacology*, 379:33-45 (1999).

Culmsee, C., et al., "NGF Mediates the Neuroprotective Effect of the $\beta_2$-adrenoceptor Agonist Clenbuterol In Vitro and In Vivo: Evidence from an NGF-Antisense Study," *Neurochemistry International*, 35:47-57(1999).

Kahn, T., et al., "Muscle Atrophy Reversed by Clenbuterol Following Chronic Spinal Cord Injury," *Regeneration R&D Service*, 88:15 p. 218. 1999.

Maltin, C.A., et al. "Clenbuterol, a $\beta$-aderenoceptor Agonist, Increases Relative Muscle Strength in Orthopaedic Patients,"*Clinical Science*, 84:651-654 (1993).

Martineau, L., et al., "Salbutamol, a $\beta_2$-adrenoceptor Agonist, Increases Skeletal Muscle Strength in Young Men," *Clinical Science*, 83:615-621 (1992).

D.M. Rapoport, et al., "Comparison of the Effects of Busiprone and Diazepam on Control of Breathing,"*Control of Breathing: Integrated*(7028-7033).

Sahibzada, N., et al., "Reversal of Morphine-Induced Apnea in the Anesthetized Rat by Drugs that Activate 5-Hydroxytryptamine $_{1A}$ Receptors," *The Journal of Pharmacology and Experimental Therapeutics*, 292:704-713 (2000).

Zeman, R.J., "Clenbuterol, a $\beta_2$-agonist, Retards Wasting and Loss of Contractility in Irradiated Dystropic *mdx* Muscle,"*The American Physiological Society*, 865-868 (1994).

Zeman, R.J., et al., "Clenbuterol, a $\beta_2$-agonist, Retards Atrophy in Denervated Muscles," *The American Physiological Society*, 152-155 (1987).

Zeman, R.J., et al., "Slow to Fast Alterations in Skeletal Muscle Fibers Caused by Clenbuterol, a $\beta_2$Receptor Agonist," *The American Physiological Society*, 726-732(1988).

Lalley, P.M., et al., "Serotonin 1A-Receptor Activation Suppresses Respiratory Apneusis in the Cat," *Neurosci. Lett.*, 172:59-62 (1994).

Berkow, R., et al., "Disorders of Muscle Stimulation," The Merck Manual of Medical Information, (Pocket Books) pp. 331-332 (1997).

Garner, S.J., et al., "Buspirone, and Anxiolytic Drug that Stimulates Respiration," *Am. Rev. of Respir. Dis.* 139:946-950 (1989).

Van Der Heijden, H.F.M., et al., "Long-term Effects of Clenbuterol on Diaphragm Morphology and Contractile Properties in Emphysematous Hamsters," *J. of Appl. Physiol.* 85(1):215-222 (1998).

Teng, Y.D., et al., "Treatment with 5HT1A Receptor Agonists Ameliorates Respiratory Abnormalities in SOD1 Mice," *Society For Neuroscience, 31st Annual Meeting*, San Diego, Calif. Nov. 10-15, 2001, Abstract 106.9.

Maltin, C.A., et al., "Clenbuterol, a $\beta$-adrenoceptor Agonist, Increases Relative Muscle Strength in Orthopaedic Patients," *Clin Sci.*, 84:651-654 (1993).

Miller, RG, et al., Riluzole for Amyothrophic Lateral Sclerosis (ALS)/Motor Neuron Disease (MND) (Review), *The Cochrane Database of Systematic Reviews*, 2: 1-23 (Art. No. CD001447) (2002).

* cited by examiner

METHOD FOR IMPROVING RESPIRATORY FUNCTION AND INHIBITING MUSCULAR DEGENERATION

RELATED APPLICATIONS

This application is a continuation of PCT Application Ser. No. PCT/US01/40291, filed Mar. 14, 2001, which claims the benefit of U.S. Provisional Application Ser. No. 60/189,241, filed Mar. 14, 2000, the entire teachings of which are incorporated herein by reference.

GOVERNMENT SUPPORT

The invention was supported, in whole or in part, by grants PO1-NS-28130 and RO1-NS-35647 from the National Institute for Health. The Government has certain rights in the invention.

BACKGROUND OF THE INVENTION

It is well known that pulmonary pathophysiology is one of the most significant factors associated with the morbidity and mortality of individuals afflicted with either acute or chronic spinal cord injuries (SCI). Furthermore, abnormalities of respiratory function and failure of the respiratory system are leading causes of mortality in the late stages of amylotrophic lateral sclerosis (ALS).

ALS (also known as Lou Gehrig's disease) is a progressive disease of the nervous system. ALS specifically and progressively damages motor neurons, and the resulting denervation of muscular tissue in turn mediates muscular degeneration (e.g., dystrophy and atrophy). More specifically, muscular degeneration results from neuronal death, which occurs primarily by apoptosis, and the resulting denervation of muscles that normally receive axons from the affected motor neurons. The progressive muscular degeneration results in deficits in somatomotor function and speech and eventually is manifest as respiratory failure. Hence, it is crucial to identify effective therapies to prevent motor death and muscular degeneration. To date, SCI- and ALS-induced respiratory abnormalities have been neither successfully managed or treated due to a lack of effective therapeutic agents.

SUMMARY OF THE INVENTION

The present invention provides a method for improving respiratory function and inhibiting muscular degeneration (e.g., dystrophy and atrophy). Alternative embodiments of the invention provide a method of inhibiting motor neuron apoptosis and the subsequent muscular degeneration associated with the denervation of muscular tissue resulting from neuron death. The methods provided herein can be used to improve the respiratory function of individuals who have abnormal respiratory function either as a consequence of a spinal cord injury or amyotrophic lateral sclerosis.

One embodiment of the invention provides a method of improving respiratory function in an individual with abnormal respiratory function comprising administering either a serotonin (5HT) receptor type 1A agonist or a Beta2-adrenergic agonist. In particular embodiments the serotonin (5HT) receptor type 1A agonist is 8-OH-DPAT. In an alternative embodiment the serotonin (5HT) receptor type 1A agonist is buspirone. In a second alternative embodiment the invention provides a method of improving respiratory function by administering a Beta2-adrenergic agonist selected from the group consisting of clenbuterol and salbutamol. An alternative embodiment of the instant invention provides a method of preventing respiratory abnormalities in an individual afflicted with ALS comprising administering a serotonin (5HT) receptor type 1A agonist in combination with a β-2 adrenergic agonist.

The invention also provides a method of inhibiting motor neuron apoptosis in an individual comprising administering a Beta2-adrenergic agonist selected from the group consisting of clenbuterol and salbutamol.

The invention further provides a method of inhibiting muscular degeneration in an individual comprising administering an agent selected from the group consisting of a serotonin (5HT) receptor type 1A agonist (e.g., 8-OH-DPAT or buspirone) or a Beta2-adrenergic agonist (e.g., clenbuterol and salbutamol). An alternative embodiment of this aspect of the invention provides a method of preventing muscular degeneration in an individual afflicted with ALS comprising administering a scrotonin (5HT) receptor type 1A agonist in combination with a β-2 adrenergic agonist.

The invention also further provides a method of inhibiting denervation of muscles in an individual who is either afflicted with ALS or suffering from a spinal cord injury comprising administering either a serotonin (5HT) receptor type 1A agonist or a Beta2-adrenergic agonist.

DETAILED DESCRIPTION OF THE INVENTION

Figure 1:
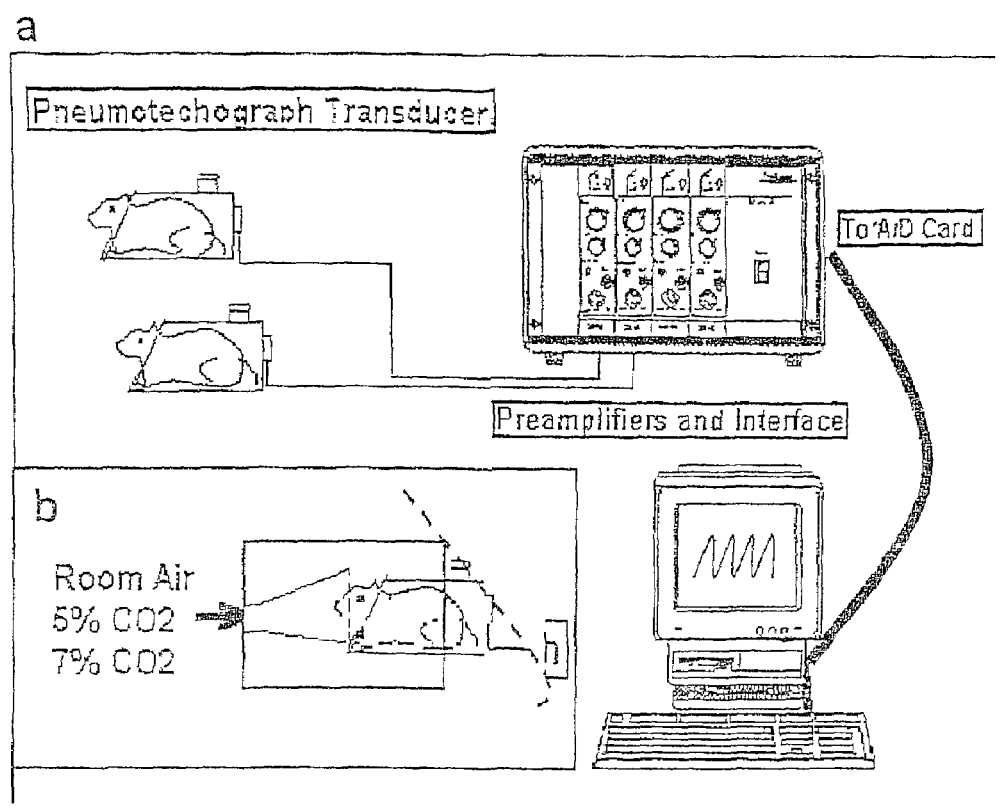
FIG. 1. Non-invasive measurements of respiratory function in conscious rats. a. Schematic presentation of the restrained head-out-plethysmograph system for rodents. b. The animals breathe from a funnel fixed in the front wall of a box made of an opaque material. The box surrounds the front-two thirds of the cylinder of the plethysmograph, and the rear outlet of the box is covered with a piece of bath towel (illustrated by a dash line). The animals are exposed to the room air for baseline recordings then to an air mixture containing 7% $CO_2$ (mixed with 60% $O_2$ and 33% $N_2$) for 5 minutes and recording of respiratory activity is continued for another 2 minutes (a total recording duration of 7 minutes). After a new baseline is obtained by allowing the animals to breathe room air for 20 minutes, the rats are allowed for other procedures and recordings determined by each experiment specifically (see Method for details).

Because of damages to the long axons of bulbospinal premotor neurons, high level injuries between lower brainstem and C4 result in pentaplegia that required immediate respirator support (Prakash, 1989). In contrast, patients with SCI between T1 and S1 have been observed for losing control of intercostal and abdominal muscles, leading to a diminished ability to generate inspiratory and expiratory movements. These patients could experience an alarming sense of difficulty breathing (dyspnea) (Prakash, 1989). Unlike high level injuries, SCI between T1 and S1 may spare some of the axonal connection between bulbospinal premotor neurons to phrenic nucleus (i.e. somatomotor neurons at C3 to C5, Feldman and McCrimmon, 1999). Hence, we believe that breathing dysfunction of such patients would be better managed with drugs that stimulate respiration. This rationale is based on that drug treatment can be easily executed in a timing manner, and it can prevent complications that frequently occur in the process of ventilator support (Mansel and Norman, 1990). However, historically respiratory disorders caused by lower thoracic SCI were much less studied in experimental models, and therefore such treatments are still not available. Recently, using a clinically relevant animal model of SCI, we reported that incomplete contusion of SCI at T8 produced significant respiratory abnormalities (Teng et al., 1998a and and 1999). The deficits consist of an abnormally lower tidal volume (Vt) and higher respiratory rate (f) in conscious rats at 24 hours and 7 days post injury (p.i.) relative to values observed prior to SCI. Moreover, T8 SCI diminished ventilatory response to the respiratory stimulating effect of 7% $CO_2$ (Teng et al., 1999). The abnormal repriatroy pattern in SCI rats is conforming to that found in patients with lower thoracic SCI (Prakash, 1989). We consequently decided to seek drug therapies for respiratory malfunctions in conscious SCI rats. We hypothesized that 8-hydroxy-2-(di-n-propylamino)tetralin (8-OH-DPAT) and buspirone, agonists of $5HT_{1A}$ receptors may improve respiratory function after contusion SCI in conscious rats, because our previous discovery showed these drugs counteracted respiratory dysfunction induced by morphine overdose (Ferreira et al., 1998).

To test this hypothesis, we used a head-out plethysmograph system (Dorato et al., 1983; Teng et al., 1999) to examine the effects of SCI at T8 on respiration in conscious rats, and the effect of treatment with 8-OH-DPAT or buspirone on respiratory deficits. For examining the specificity of the beneficiary effect of 8-OH-DPAT on respiratory function after SCI, we also conducted a time-course study for 8-OH-DPAT. In addition, the specific antagonism of 8-OH-DPAT effects was evaluated by pre-treating SCI rats with 4-(2'-methoxyphenyl)-1-[2'-[N-(2"-pyridinyl)-p-iodobenzamido]ethyl]piperazine (p-MPPI), an in vivo competive antagonist of $5HT_{1A}$ receptors, to determine if the effects of 8-OH-DPAT could be prevented.

In this study, we have fulfilled our task to examine whether $5HT_{1A}$ receptor agonistic drugs, 8-OH-DPAT and buspirone (Middlemiss and Fozard, 1983; Hamon et al., 1986; Hoyer and Schoeffter, 1991) could reverse respiratory malfunctions resulting from traumatic SCI. We first demonstrate that incomplete contusion injury at T8 causes significant abnormalities of respiration, which is consistent with previous findings from others and ourselves (Baker et al., 1979; Teng et al., 1998a and 1999). Respiratory disorders that are discerned in conscious rats at 24 hours and 1 week after SCI include rapid and shallow pattern of repiration under baseline conditions (i.e. room air ventilation), and a dramatically diminished ventilatory response to breathing $CO_2$ that is abnormally concentrated (i.e. 7% vs the physiological 0.4%). A single treatment of 8-OH-DPAT administered i.p. at 24 hours after injury counteracts SCI-induced respiratory abnormalities in a time-related manner. Identical results are also achieved by 8-OH-DPAT treatment at 7 days p.i. At 24 hours p.i., pre-injury levels of respiratory parameters are also reinstated by treatment of buspirone, a partial $5HT_{1A}$ receptor agonist (Hoyer and Schoeffter, 1991). In addition, pre-treatment of the SCI rats wit p-MPPI, a specific antagonist of $5HT_{1A}$ receptors (Thielen et al., 1990) prevents 8-OH-DPAT from counteracting SCI-induced respiratory abnormalities. The results suggest that the beneficial effect of 8-OH-DPAT and buspirone in treating SCI-triggered respiratory deficits is mediated through $5HT_{1A}$ receptors.

This is the first report that systematic administration of $5HT_{1A}$ agonistic drugs promptly and efficiently restores respiratory abnormalities resulting from contusion SCI to normal. Nevertheless, previous reports from other groups show that 8-OH-DPAT and buspirone are capable to reverse respiratory depression such as an apneustic respiration (an abnormal breathing pattern characterized by an over-elongated inspiration phase). The apneusis was induced by antagonist (i.e. MK-801 and Ketamine) of the NMDA-subtype receptors of the excitatory amino acids (Lalley et al., 1994; Wilken et al., 1997), pentobarbital (Lalley et al., 1994), or hypoxia (Lalley et al., 1994). Our group has also shown that 8-OH-DPAT and buspirone administered i.v. counteract respiratory depression (mostly, apnea) triggered by morphine overdose (Ferreira et al., 1998). With detailed data generated exclusively from anesthetized animals, those studies have illuminated the possibility to use $5HT_{1A}$ agonistic drugs to treat respiratory depression in conscious animals.

SCI in general severely damages respiratory function (Prakash, 1989). Moreover, most of the morbidity and mortality at both acute and chronic stages after human SCI is due to respiratory dysfunction (Slaok and Shuoart, 1994; Frankel et al., 1998). Thus, therapeutic strategies are urgently needed to improve respiration after SCI. However, historically there has been very limited experimental information on SCI-resulted respiratory malfunction, still less investigations for potential drug treatments to reinstate proper respiration. A main reason for this reality is that little has been done to examine effects of SCI on respiration in clinically relevant animal models. Recently, by using a plethysmograph, wer were able to evaluate respiration in conscious rats before and repeatedly after a standardized SCI (Teng et al., 1998a and 1999). Furthermore, in the current study, we successfully demonstrate that both 8-OH-DPAT and buspirone can restore SCI-induced respiratory abnormalities to normal. Our finding is consistent with an earlier report: buspirone taken orally (8 mg/day) reverses apneusis in a child after a surgery to remove a brainstem tumor (Wilken et al., 1997).

The rapid and shallow respiratory pattern that was found in rats after SCI was associated with the loss of ventral motor neurons at and near the T8 injury site (Teng et al., 1998 b and 1999). Ventral motoneurons at thoracic levels innervate both the intercostal (motneurons at $T_1-T_{13}$) and abdominal muscles (motoneurons at $T_5-L_3$; Holstege, 1991). The intercostal muscles have an important respiratory function and their paralysis causes significant alteration in the elastic properties of the lungs and reduces the outward elastic recoil of the rib cage (Gibson et al., 1977; Troyer and Heilporn, 1980). Therefore, patients with quadriplegia caused by SCI below C5 with detectable intercostal electromyographic activity had much better respiratory function than those who lost it (Troyer and Heilporn, 1980). Consequently, respiratory impairments were expected for T8 SCI due to loss of thoracic motoneurons, as well as the loss of white matter containing supraspinal control pathways to respiratory motoneurons below the injury site. Indeed, we have demonstrated that basic fibroblast growht factor (FGF2), a neurotrophic factor administered into the injury epicenter at 5 minutes p.i. prevents respiratory abnormalities from happening through reducing neuronal losses (Ten et al., 1999).

The mechanism(s) and site(s) whereby $5HT_{1A}$ agonistic drugs act to improve respiration following SCI remain to be further investigated. However, the beneficial effects of 8-OH-DPAT and buspirone on p.i. respiration that we observed can not be owned to possible neuronal protection for two reasons. First, by 24 hours and 7 days p.i., major neuronal loss at or near injury epicenter already completed in the spinal cord (Noble and Wrathall, 1985 and 1989; Crowe et al., 1997; Teng et al., 1998b). Correspondingly, effects of 8-OH-DPAT in the current study display as a time-dependent phenomenon (FIG. 3), which is contrasted with that of FGF2 (Teng et al., 1999). Secondly, there are no evidences that $5HT_{1A}$ agonistic drugs spare neurons or neural tissues after traumatic injury. Hence, another possibility for these drugs to work is to act on surviving spinal motoneurons. Yet published data concerning whether $5HT_{1A}$ agonists postsynaptically stimulate spinal somatomotor neurons do not support this notion. Jackson and White (1990) reported that iontophoretically delivered 8-OH-DPAT into the ventral horn inhibited the glutamate-evoked firing of motoneurons while similarly applied agonists for $5HT_{1B}$, $5HT_{1C}$ and $5HT_2$ augmented it. In a SCI-related study, increased serotonergic inervation of phrenic motoneurons (located at C3 to C5 of the cervical spinal cord) is identified to be accountable for long-term facilitation of respiratory motor output triggered by episodic hypoxia at 28 days after cervical dorsal rhizotomy (Kinkead et al., 1998). Again, the effect is mediated by $5HT_2$ receptors in this case since it is blocked by pretreatment of ketanserin, a $5HT_2$ antagonist (Bach and Mitchell, 1996; Kinkead et al., 1998). Thus, it is conceivable that in our study 8-OH-DPAT and buspirone are not acting on spinal motoneurons. In fact, sites of action for the respiratory effect of $5HT_{1A}$ agonists were confined within the brainstem to certain degree in literatures describing their cardiovascular effects and their counteraction mechanisms on apneusis. Work by Fozard et al., (1987) show that in conscious, spontaneous hypertension rats, 8-OH-DPAT causes dose-related falls in blood pressure and heart rate. The same effects are not observed in pithed rats. Moreover, the response to 8-OH-DPAT is blocked by intracisternal injection of 8-MeO-CIEPAT, an irreversible $5HT_{1A}$ receptor antagonist (Fozard et al., 1987). Another report reveals that application of 5-methoxy-N,N-dimethyl-trptamine, a $5HT_{1A}$ agonist to the dorsal surface of the medulla oblongata reverses apneusis produced by pentobarbital (Lalley, 1994). Under this circumstance, the most feasible target for the drug is neurons in the dorsal respiratory group of the medulla. In our earlier study of $5HT_{1A}$ agonist reversal of morphine-induced apnea (Ferreira et al., 1998), we believe that $5HT_{1A}$ agonist drugs may act directly on brainstem respiratory rhythm generating centers: the Pre-Botzinger Complex to re-start respiration which was suppressed by morphine (Smith et al., 1991). Indeed, it has been reported that direct application of 5HT to the medulla area embodying Pre-Botzinger Complex increments the frequency of burst discharge of those neurons (Al-Zubaidy et al., 1996; Onimaru et al., 1998). Further, our present data indicate that $5HT_{1A}$ agonists improve respiration by directly stimulating respiratory neurons and not by other mechanisms such as augmenting sensitivity to $CO_2$. Table 2 exhibits that 8-OH-DPAT treatment does not affect ventilatory response to 7% $CO_2$ in normal rats. Thus, despite we did not directly investigate the mechanism(s) and location(s) for $5HT_{1A}$ agonists to improve SCI-triggered respiratory dysfunction, our data from 8-OH-DPAT time-course and p-MPPI antagonism experiments clearly suggest that the effect is mediated through $5HT_{1A}$ receptors. Furthermore, existing evidences indicate that the most likely site(s) for 8-OH-DPAT buspirone to restore p.i. respiratory function to normal is respiratory neurons in the brainstem. Thereafter, we postulate that by stimulating the brainstem respiratory premotoneurons both pre- and post-synoptically, $5HT_{1A}$ agnistic drugs can increase the activity of phrenic motoneurons which are essentially undamaged by T8 injury. Subsequently, the enchanced diaphragm contraction can compensate activity loss of intercostal muscles resulting from neuronal death in the thoracic spinal cord. We're currently testing this hypothesis by comparing pre-8-OH-DPAT phrenic nerve outflow to that recorded after drug administration in anesthetized rats at different time points p.i.

Our data have provided the first description of the reversal of SCI-induced respiratory abnormalities in conscious rats by systemic administration of $5HT_{1A}$ receptor agonistic drugs. The study also indicates that the respiratory improving effect is generated through specific interaction between these drugs and $5HT_{1A}$ receptors. Morever, we have shown that buspirone, a human clinical drug is highly effective for restoring respiratory function to normal after contusion SCI. In conclusion, our results demonstrate that $5HT_{1A}$ receptor agonistic drugs can be used to improve respiratory function in conscious rats subsequent to SCI.

Figure 6:
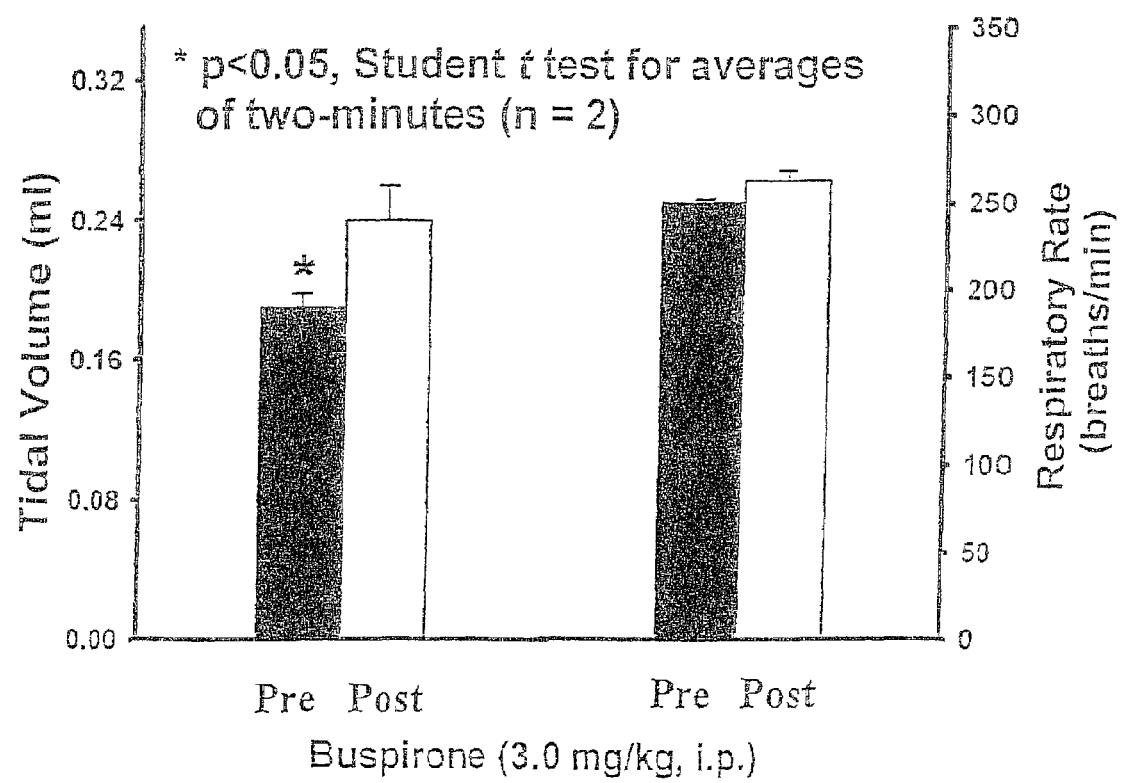
FIG. 6. A schematic representation of the effects of the intraperitoneal administration of buspirone at a dose of 3.0 mg/kg on the respiratory function (e.g., tidal volume and respiratory rate) of SOD1 mice.
Figure 7:
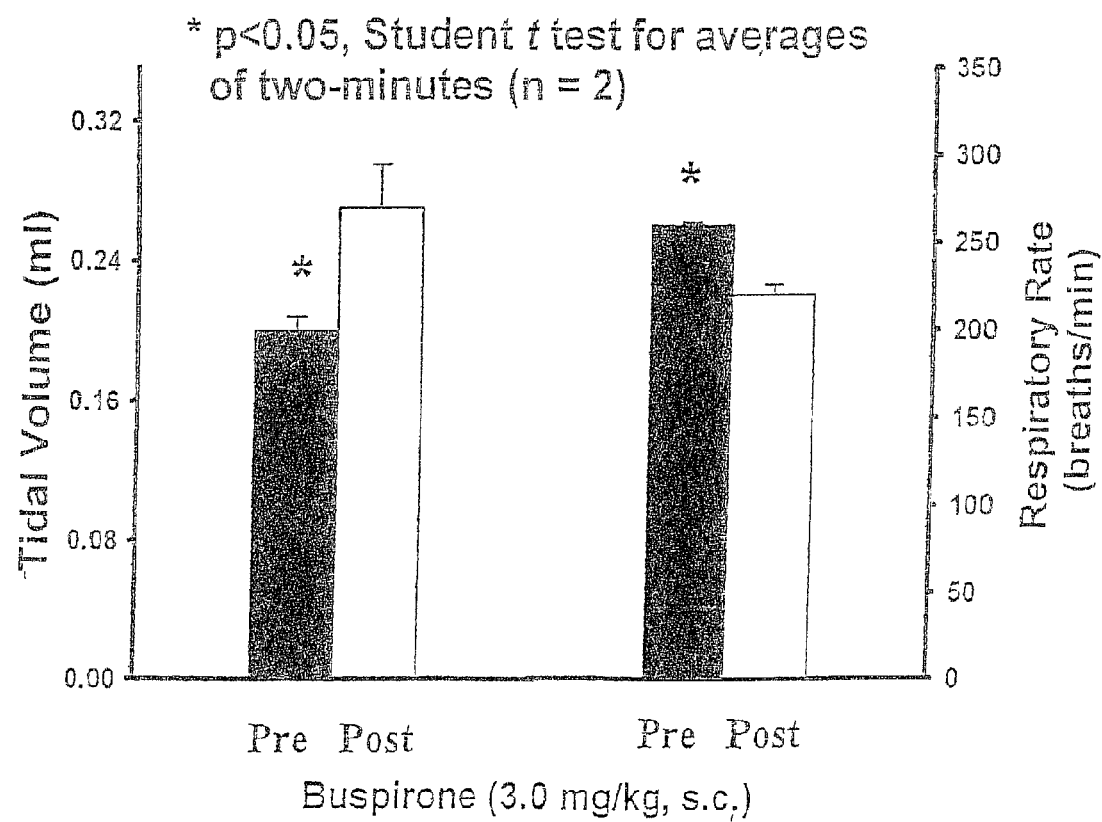
FIG. 7. A schematic representation of the effects of the subcutaneous administration of buspirone at a dose of 3.0 mg/kg on the respiratory function (e.g., tidal volume and respiratory rate) of SOD1 mice.

The data presented herein demonstrate that specific agonists of serotonin (5HT) receptor type 1A such as 8-OH-DPAT and buspirone counteract (e.g., ameliorate) abnormalities mediated by motoneuron loss in spinal cord injury (Teng et al., 1999;2000). It is well known that the same category drugs can ameliorate respiratory suppression that is caused by morphine overdose, glutamate antagonists, and sleep disorders (Ferreira et al., 1998; Rappaport et al., 1988). Considering the fact that ALS-related respiratory abnormalities are also triggered by muscle dysfunction due to denervation, we determined whether buspirone could mitigate respiratory deficits in SOD1 mice (a mutant mouse model for familial ALS, an inherited form of ALS), (Example 6). The data summarized in FIGS. 6 and 7 demonstrates that buspirone treatment significantly increases tidal volume and simultaneously reduces respiratory frequency. These results clearly demonstrate that 5HT 1A agonists can be used to improve respiratory abnormalities that are resulted from ALS pathophysiology.

While not wishing to be bound by theory, it is believed that 5HT 1A agonists improve respiration through their proper stimulation of respiratory premotoneurons (i.e. neurons in brain stem). Since these drugs are currently used clinically for anxiolytic purpose we think that they can be applied to ameliorate late stage ALS patients' respiratory stress (e.g. ALS patients at late stage often complain for lack of air) as well as their emotion imbalance. Further, we hypothesize that proper stimulation of motoneurons (i.e. neurons in brain stem and spinal cord) may delay their degeneration caused by ALS pathology and pathophysiology. This opportunity will be further enhanced by co-application of β2-adrenergic agonists because the later can preserve muscle function and increase expression of neural trophic factors. Hence, it is very likely that synergistic or additive effects may be observed between 5HT 1A agonists and β2-adrenergic agonists in mitigating ALS symptoms and retarding development of ALS pathology. Together, they can form a new strategy to treat ALS, improve life quality, and elongate life span for ALS patients.

β2-Adrenergic agonists are highly potential counteracting drugs to for the muscle fiber degeneration, since these compounds have been demonstrated to increase muscel strength by either induce muscle hypertrophy (Bardsley et al., 1992; Emery et al., 1984; Rothwell and Stock, 1985) or retarding denervation atrophy (Maltin et al., 1987; Zeman et al., 1987). In terms of general pharmacology, clenbuterol is the most widely studied agent among the β2-adrenergic agonists. Clenbuterol is an extemely potent and selective β2-adrenergic agonist with a long duration of action and has been shown to increase muscle mass in innervated (Agbenyega et al., 1990; Emery et al., 1984; maltin et al., 1987), denervated (Maltin et al., 1986, Zeman et al., 1988), and dystrophic muscles (Rothwell and Stock, 1985; Zeman et al., 1994). Long-term studies show that clenbuterol given orally 1.0–1.5 mg/kg body weight/day significantly increase soleus (SOL) weight and SOL muscle weight to body weight ratio in both normal control mice and muscular dystrophic (i.e. mdx mutant mice)mice during a one year treatment period. In addition, there is a 22% increase in myosin concentration of mdx diaphram (DIA), correlating well with enhanced normalized active tension in mdx DIA. Another long-term study reveals that clenbuterol increases absolute and relative muscle masses in mdx mice. The larger SOL muscle also produces larger absolute forces. Twitch contraction time is significantly faster following clenbuterol administration, supported by fiber-type transitions toward fast-twitch fibers. On the other hand, in chronically spinal cord injured rats, enervation-caused muscle atrophy is also reserved by oral administration of clenbuterol (Khan et al., 1999; Zeman et al., 1999). Furthermore, clenbuterol is demonstrated to be neuroprotective (i.e. reducing the cortical infarct volume in Long-Evans rats as measured 7 days after permanent occlusion of the middle cerebral artery) by increasing mRNA expression for neural trophic factors such as nerve growth factor (NGF), basic fibroblast growth factor (bFGF), and transforming growth factor-beta 1 (TGH-beta1) in cortical and hippocampal tissue (i.e. neurons and glial cells; Culmsee et al., 199a and b). This kind of neural growth factor up-regulation is thought as the mechanism for the inhibition effects of clenbuterol on neuronal apoptsis.

Although what causes neuronal death in ALS is still not completely understood, we do know that most neurons die from apoptosis in ALS. We also know that neural growth factors such as NGF and bFGF can inhibit neuronal apoptosis both in vitro and in vivo. Thus, it is reasonable to hypothesize that β2-adrenergic agonists such as clenbuterol can be used to prevent or reduce neuronal loss of ALS. In addition, the anti-muscle degeneration effects of clenbuterol, especially its robust effect on enervation-related muscular dystrophy may significantly minimize the impacts fo the direct killer of ALS: loss of muscular function. As clenbuterol is related to a number of compounds that are currently used to treat asthmatics, its lont-term use may not be associated with a long list of side effects. Indeed both clenbuterol (Maltin et al., 1993) and another β2-adrenergic agonist, salbutamol (Martineau et al., 1992), have recently been used in investigations on human subjects for their effects on muscles. Therefore, clenbuterol and other β2-adrenergic agonists may become successful therapeutic agents for ALS patients who currently do not have any effective treatments.

The following Examples are offered for the purpose of illustrating the present invention and are not to be construed to limit the scope of the invention.

METHODS AND MATERIALS USED IN EXAMPLES

Spinal Cord Injury.

Female Sprague-Dawley rats (250–280 g and 360–390 g; Taconic, Germantown, N.Y.) were anesthetized with 4% chloral hydrate (360 mg/kg, i.p.). An incomplete spinal courd contusion injury was produced at T8 with a weight drop device (10 g×2.5 cm) as previously described (Wrathall et al., 1985). After SCI, manual expression of bladders was performed twice daily until a reflex bladder was established. Animal care also included housing the rats in pairs to reduce isolation-induced stress, maintaining ambient temperature at 22–25° C., and using highly absorbent bedding. No prophylactic antibiotics were given.

Monitoring of Respiratory Parameters by Plethysmograph.

Experiments were conducted in unanesthetized, awake, spontaneously breathing rats at 24 hours prior to SCI, at 24 hours p.i. and weekly afterwards at 1,2,3, and 4 weeks p.i. (1) Acclimatization of the Animals. We found that correct plethysmograph-recordgn of respiratory parameters of conscious rats required animal training for acclimatization. Animals were placed in the body cylinder of the plethysmograph (FIG. 1a) for 60 minutes per day for at least 5 days. This procedure led them to become used to the environment. Upon acclimatization, rats remained quietly in the cylinder allowing for the acquisition of data without physical signs of stress (i.e. defecation, urination, and bloody secretions in the eyes and nose) and motion artifacts. (2) Non-Invasive Measurements of Respiratory Rate, Tidal Volume and Minute Ventilation. Non-invasive measurements of respiratory function in conscious rats were performed with a restrained head-out plethysmograph specially designed for rodents (BUXCO Electronics, Inc., Sharon, Conn.) (FIG. 1a). The plethymograph apparatus has a neck seal that prevents leakage of air from between the animal's neck and the plethymograph opening. Displacement of the thoracic wall produced by the animal's respiratory movements causes changes in the cylinder pressure, which results in air flowing across a pneumotachograph located on the wall of the cylinder. The pressure drop across the pneumotachograph is measured with a pressure transducer and is proportional to the flow. This signal is amplified and integrated into volume. From measurements of volume and flow, a computer and appropriate software provides respiratory parameters, such as respiratory rate (f), tidal volume (Vt), minute ventilation (Ve), peak inspiratory flow, peak expiratory flow, inspiratory time (Ti), expiratory time (Te), and accumulated volume. An additional opening on the wall of the box allows volume calibration by injecting and removing air from the box with a calibrated syringe.

The noise level in the laboratory was kept to a minimum in order not to startle the animals. Further, the animals were visually isolated from the investigators by means of a chamber made of an opaque material that surrounded and covered the front-end of the body plethysmograph (FIG. 1b). Baseline recordings lasted for 4 minutes. (3) Measurement of Ventilatory Response to Carbon Dioxide. For measurement of the ventilatory response to $CO_2$, animals were exposed to air containing 7% $CO_2$. The animals breathed from a funnel fixed in the front wall of a chamber made of an opaque material (FIG. 1b). The animals were exposed to the gas mixture containing 7% $CO_2$ (mixed with 60% $O_2$ and 33% $N_2$) for 5 minutes with recording of respiratory activity for another 2 minutes (a total recording duration of 7 minutes).

Drug Administration.

The $5HT_{1A}$ receptor agonists, 8-OH-DPAT and buspirone (both purchased from RBI, Natick, Mass.) were dissolved in 0.9% saline (pH adjusted to 7.4). Both agonists were administered intraperitoneally in 0.5 ml final injecting volume per rat (i.p.) and in doses of 250 µg/kg for 8-OH-DPAT and 1.5 mg/kg for buspirone respectively. The $5HT_{1A}$ receptor antagonist, p-MPPI (RBI, Natick, Mass.) was also dissolved in 0.9% saline and given i.p. in a dose of 3 mg/kg (pH 7.4 and final volume of 0.5 ml). The doses of the above drugs were decided based on our earlier report that demonstrated that $5HT_{1A}$ agonists could reverse morphine-induced respiratory depression (Ferreira et al., 1998). Vehicle solution (VEH) was 0.9% saline and also injected at i.p. (pH 7.4; volume: 0.5 ml/rat).

Experimental Protocol.

SCI surgical procedures were performed only after animals finished at least 5 days plethysmograph acclimatization (see above) and at 24 hours after plethysmograph data acquisition for pre-injury respiratory parameters. Test of functional deficits were performed at 24 hours prior to SCI, and at 24 hours and weekly afterwards for 4 weeks p.i. to determine a proper degree of SCI was achieved (Gale et al., 1985; Basso et al., 1995).

Baseline respiratory function was measured under room air ventilation and after the animal was stabilized inside a boy cylinder (FIGS. 1a and b) for 30 minutes at each time point prior to SCI and after injury. Immediately following the evaluation of baseline respiration, the animals were let to breathe air containing 7% $CO_2$ for 7 minutes to monitor their ventilatory response to $CO_2$ stimulus (Teng et al., 1998a and 1999). For VEH and 8-OH-DPAT studies, at 24 hours p.i., respiratory function of a SCI rat was first evaluated by plethysmograph for baseline performance as well as respiratory response to 7% $CO_2$ challenge. Twenty-four minutes post the end of $CO_2$ breathing, the rat was removed from the body cylinder (FIG. 1a) after a new baseline was recorded for 4 minutes. The animal was then injected with saline VEH (0.5 ml, i.p.) and immediately put back into the cylinder in a smooth manner for continuing respiratory monitoring (the procedure took about 1.2 minutes average). Baseline respiration (i.e. under room air ventilation) was examined for another 10 minutes, and at the end, ventilatory response was evaluated when the animal was challenged by 7% $CO_2$ for 7 minutes. Twenty-four minutes post the end of $CO_2$ stimulus (including a recording of a new baseline for 4 minutes), the rat was again taken out from the body cylinder subsequent to a new baseline recording for 4 minutes. Therewith the animal was injected with 8-OH-DPAT (250 µg/kg in 0.5 ml, i.p.), and immediately sent back into the cylinder for continuing respiratory monitoring (the procedure took about 1.2 minutes in average). Following the drug administration, baseline respiration (i.e. under room air ventilation) was examined constantly for another 23 minutes. At the end of the $23^{rd}$ minute, ventilatory response was evaluated once more when the rat was challenged with 7% $CO_2$ for 7 minutes. Similar procedures for the 8-OH-DPAT study were repeated at 7 days p.i. except that no saline VEH treatment was given. In the time-course study for the respiratory effect of 8-OH-DPAT, recordings of baseline respiratory function (for 4 minutes) and ventilatory response for 7% $CO_2$ (for 7 minutes) were repeated hourly for up to 5 hours after the administration of 8-OH-DPAT. In experiments of p-MPPI antagonism of 8-OH-DPAT effects, p-MPPI (3 mg/kg in 0.5 ml/rat, i.p.) was given at 20 minutes before the administration of 8-OH-DPAT. Baseline respiratory function was examined beginning at 4 and 18 minutes after p-MPPI injection (each lasted for 2 minutes). Baseline recording was performed again at 4 and 8 minutes following i.p. 8-OH-DPAT (each lasted for 2 minutes), and at the end of the $10^{th}$ minute after 8-OH-DPAT, ventilatory response to breathing 7% $CO_2$ was measured. For the study of the buspirone effects, similar sequential procedures as those in the 8-OH-DPAT experiment were followed. However, the 7% $CO_2$ challenge was given at 10 minutes after i.p. injection of buspirone (1.5 mg/kg in 0.5 ml), and neither time-course nor antagonism study was performed for buspirone.

All animals survived the study. Experimental data are expressed as mean I SEM. Statistical significance was defined at the p<0.05 level. The statistical tests used are described below and also specified in the figure legends. All experimental procedures were carried out in strict accordance with the Laboratory Animal Welfare Act, Guide for the Care and Use of Laboratory Animals (NIH, DHEW Publication No. 78-23, Revised 1978) after review and approval by the Animal Care and Use Committee of Georgetown University.

Statistical Analyses.

Respiratory data were analyzed statistically using repeated measures ANOVA, followed by Tukey's or Dunn's test for multiple comparisons between groups used in previous studies (e.g., Wrathall et al., 1994; Teng and Wrathall, 1997; Teng et al., 1999). The same statistical tests were used for analyzing respiratory data from drug treatment studies.

Contusion spinal cord injury (SCI) at T8 produces respiratory abnormalities in conscious rats breathing room air challenged with $CO_2$. In seeking ways to improve respiration in SCI animals, we tested drugs that stimulate serotonin 1A ($5HT_{1A}$) receptors, based on our findings that those agents can counteract respiratory depression produced by morphine overdose. Respiratory function was measured with a head-out plethysmograph system in conscious rats.

Example 1

Treatment with the Serotonin 1A Receptor ($5HT_{1A}$) Agonist 8-OH-DPAT Improves Respiratory Function in Spinal Cord Injured Rats Respiratory function was evaluated when rats were breathing room air for the data baseline respiration. In addition, rats were challenged with air mixtures containing 7% $CO_2$, as described in Methods. This was done to determine the effect of SCI on the central chemoreceptor-mediated respiratory responses to high concentration of $CO_2$.

Twenty-four hours after we examined respiratory function in rats prior to injury to establish normal parameters, rats were subjected to SCI. At 24 hours p.i. and 7 days p.i., all SCI rats were tested behaviorally for their hindlimb reflexes and coordinated use of hindlimbs, including a detailed examination of open field locomotion (Gale et al., 1985; Basso et al., 1995; Wrathall et al., 1994; Teng and Wrathall, 1997). We found that behavioral deficits proper to this degree of SCI as well as post-injury time points (i.e. at 24 hours or 7 days p.i.; Wrathall et al., 1994; Teng and Wrathall, 1997) existed in all SCI rats (data not shown). Further, no significant differences in behavioral deficits were found among the SCI rats (repeated measures ANOVA, P>0.05). Thereupon SCI rats were randomized to receive either 8-OH-DPAT (250 µg/kg in 0.5 ml/rat, i.p.), a $5HT_{1A}$ agonistic drug (Middlemiss and Fozard, 1983; Harmon et al., 1986) or VEH solution (0.5 ml/rat, i.p.). The administration was started at 24 minutes after the end of the first $CO_2$ challenge: following a recording of a new baseline for 4 minutes (see Methods for details).

Figure 2:
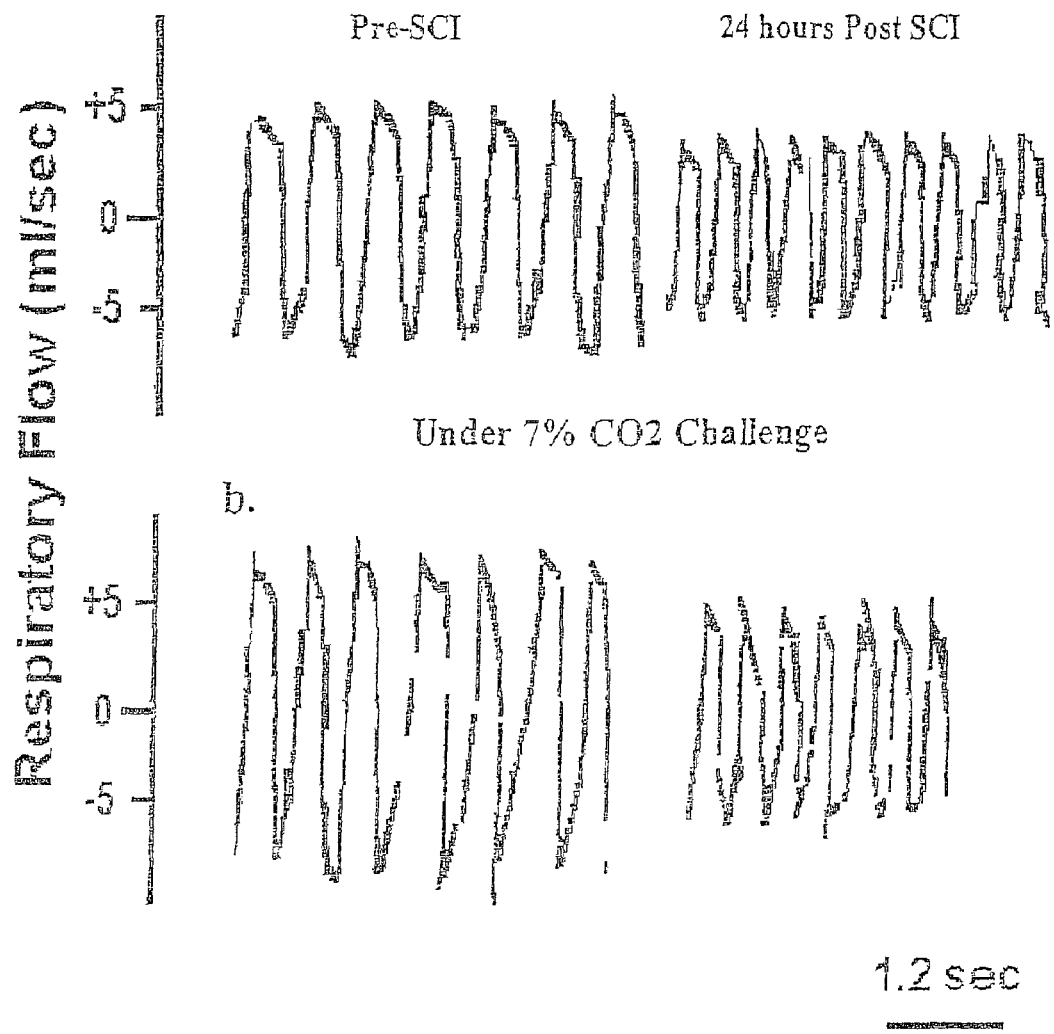
FIG. 2. Effects of incomplete contusive SCI at T8 on respiratory function at 24 hours post injury. a. Plethysomograph tracings of respiratory flow rate (unit: ml/sec) obtained from conscious rats breathing room air 24 hours prior to spinal cord injury and 24 hours after injury; b. Plethysmograph tracings of respiratory flow rate (unit: ml/sec) obtained from conscious rates breathing air containing 7% $CO_2$ 24 hours piro to spinal cord injury and 24 hours after injury.

Contusion SCI at thoracic 8 vertebral level caused a significant decrease in Vt along with a significant increase in f at 24 hours p.i. (Table 1; FIG. 2) and 7 days p.i. (Table 1) compared to pre-injury respiratory parameters. Rats at 24 hours and 7 days after SCI demonstrated a pattern of breathing which was more shallow and rapid than prior to injury (FIG. 2). Our data demonstrated again that SCI at T8 produced significant impairments on respiration as evaluated in conscious rats (Teng et al., 1999). At 24 hours after SCI, while VEH treatment did not alter the abnormal respiratory pattern resulting from SCI (Table 1), 8-OH-DPAT administration promptly and successfully reversed the injury-triggered respiratory abnormalities. For example at 22 minutes after i.p. injection of 8-OH-DPAT, Vt was changed significantly from post-SCI level of 0.66±0.03 to 0.80±0.06 (unit: ml; P<0.05, repeated measures ANOVA with Tukey's procedure; Table 1), a value that was statistically indistinguishable compared to Vt prior to SCI (0.90±0.02, unit: ml; P>0.05, repeated measures ANOVA with Tukey's procedure; Table 1). At the same time, treatment of 8-OH-DPAT also brought f that was significantly increased by SCI (131.6±5.7 vs 90.8±3.7, unit: breaths/min: P<0.05, repeated measures ANOVA with Tukey's procedure; Table 1) back to normal (98.5±3.7, units: breaths/min; P>0.05, repeated measures ANOVA with Tukey's procedure; Table 1). Nonetheless, treatment with 8-OH-DPAT did initially drive f even higher than the original p.i. f levels, which lasted for about 20 minutes (Table 1; some data not shown). The decrease in Vt and increase in f presented till 7 days p.i. (Table 1). Once again, 8-OH-DPAT treatment restored this abnormal pattern of breathing to normal at 7 days p.i. (Table 1). Vt and f were recovered to normal starting at 14 days after injury (n=2, data not shown), consistent with what we reported previously for the chronic recovery of respiratory function occurring in this model of SCI (Teng et al., 1999).

The SCI rats showed a dramatic decrease in the ventilatory response to $CO_2$. The Ve when breathing air containing 7% $CO_2$ was significantly decreased at 24 hours p.i. as compared to that observed prior to the injury (161.7±14.9 vs 250.4±17.0, unit: ml/min; P<0.05, repeated measures ANOVA with Tukey's procedure; Table 1). The abnormalities of ventilatory response to 7% $CO_2$ were still significant at 7 days p.i. (Table 1). Beginning at 14 days p.i., the response to 7% $CO_2$ recovered to pre-injury levels (data not shown). The severely impaired ventilatory response to 7% $CO_2$ in the SCI animals at 24 hours and 7 days after SCI was normalized by the treatment of 8-OH-DPAT in the same rats that did not show any significant Ve improvement following VEH administration (Table 1).

TABLE 1

Respiratory Parameters of Conscious Rats That Received
Systemic Saline and 8OH-DPAT at 24 Hours after SCI

| Experimental Group | Prior to SCI and Treatments | | 24 h after T8 SCI | | 24 h p.i.: Saline (i.p.) | 24 h p.i.: 7% CO2 post Saline (i.p.) |
|---|---|---|---|---|---|---|
| | Baseline | 7% CO2 | Baseline | 7% CO2 | Baseline | Baseline |
| T8 SCI Rats That Received 8OHDPAT (250 μg/kg, i.p.) (n = 5) | Ti 0.20 ± 0.01<br>Te 0.50 ± 0.03<br>Tv 0.90 ± 0.02<br>f 90.8 ± 3.70<br>Ve 81.6 ± 3.94 | 0.18 ± 0.01<br>0.22 ± 0.01<br>1.64 ± 0.09<br>153.5 ± 7.59<br>250.4 ± 17.0 | Ti 0.20 ± 0.01<br>Te 0.28 ± 0.01↓<br>Tv 0.66 ± 0.03↓<br>f 131.6 ± 5.7↑<br>Ve 86.5 ± 6.42 | 0.17 ± 0.01<br>0.25 ± 0.03<br>1.09 ± 0.03↓<br>148.0 ± 10.9<br>161.7 ± 14.9↓ | Ti 0.19 ± 0.01<br>Te 0.34 ± 0.03↓<br>Tv 0.68 ± 0.03↓<br>f 125.4 ± 5.6↑<br>Ve 85.9 ± 6.90 | Ti 0.16 ± 0.01<br>Te 0.26 ± 0.03<br>Tv 1.04 ± 0.07↓<br>f 150.0 ± 9.8<br>Ve 157.6 ± 17.5↓ |

| Experimental Group | 24 h p.i.: Pre-8-OH-DPAT Baseline | 24 h p.i.: 3 & 4 min post 8-OH-DPAT (250 μg/kg, i.p.) Baseline | 24 h p.i.: 21 & '22 min post 8-OH-DPAT Baseline | 24 h p.i.: 7% CO2 at 24 min after 8-OH-DPAT 7% CO2 |
|---|---|---|---|---|
| T8 SCI Rats That Received 8OHDPAT (250 μg/kg, i.p.) (n = 5) | Ti 0.18 ± 0.01<br>Te 0.31 ± 0.02↓<br>Tv 0.67 ± 0.02↓<br>f 125.6 ± 3.6↑<br>Ve 83.8 ± 3.8 | Ti 0.19 ± 0.01<br>Te 0.25 ± 0.02↓<br>Tv 0.96 ± 0.08<br>f 155.5 ± 8.7↑<br>Ve 149.9 ± 15.6↑ | Ti 0.18 ± 0.01<br>Te 0.47 ± 0.02<br>Tv 0.80 ± 0.06<br>f 98.5 ± 5.18<br>Ve 81.3 ± 10.9 | Ti 0.17 ± 0.01<br>Te 0.18 ± 0 01<br>Tv 1.52 ± 0.08<br>f 175.9 ± 9.7<br>Ve 267.5 ± 21.8 |

| Experimental Group | 7 days after T8 SCI (n = 3) | | 7 d p.i.: 3 & 4 min post 8-OH-DPAT | 7 d p.i.: 21 & 22 min post 8-OH-DPAT | 7 d p.i.: 7% CO2 at 31' & 32' post 8-OH-DPAT |
|---|---|---|---|---|---|
| | Baseline | 7% CO2 | Baseline | Baseline | 7% CO2 |
| T8 SCI Rats That Received 8OHDPAT (250 μg/kg, i.p.) (n = 5) | Ti 0.18 ± 0.01<br>Te 0.28 ± 0.03↓<br>Tv 0.72 ± 0.03↓<br>f 134.4 ± 10.2↑<br>Ve 96.3 ± 5.1 | 0.18 ± 0.00<br>0.18 ± 0.02<br>1.39 ± 0.08↓<br>167.3 ± 11.7<br>253.6 ± 41.3 | Ti 0.16 ± 0.01<br>Te 0.26 ± 0.03↓<br>Tv 1.11 ± 0.05<br>f 155.2 ± 8.9↑<br>Ve 172.1 ± 17.1↑ | Ti 0.15 ± 0.01<br>Te 0.32 ± 0.02↓<br>Tv 0.79 ± 0.04<br>f 131.7 ± 7.7↑<br>Ve 103.0 ± 2.1↑ | Ti 0.16 ± 0.01<br>Te 0.17 ± 0.01<br>Tv 1.79 ± 0.35<br>f 184.6 ± 6.6↑<br>Ve 327.2 ± 53.7↑ |

↑ or ↓: Significantly higher or lower compared to pre-SCI values; $P < 0.05$, one way ANOVA followed by Tukey's or Dunn's test for multiple comparisons.

Example 2

Time-Course Study of the Effects of 8-OH-DPAT on Minute Ventilation ($V_e$)

Figure 3:
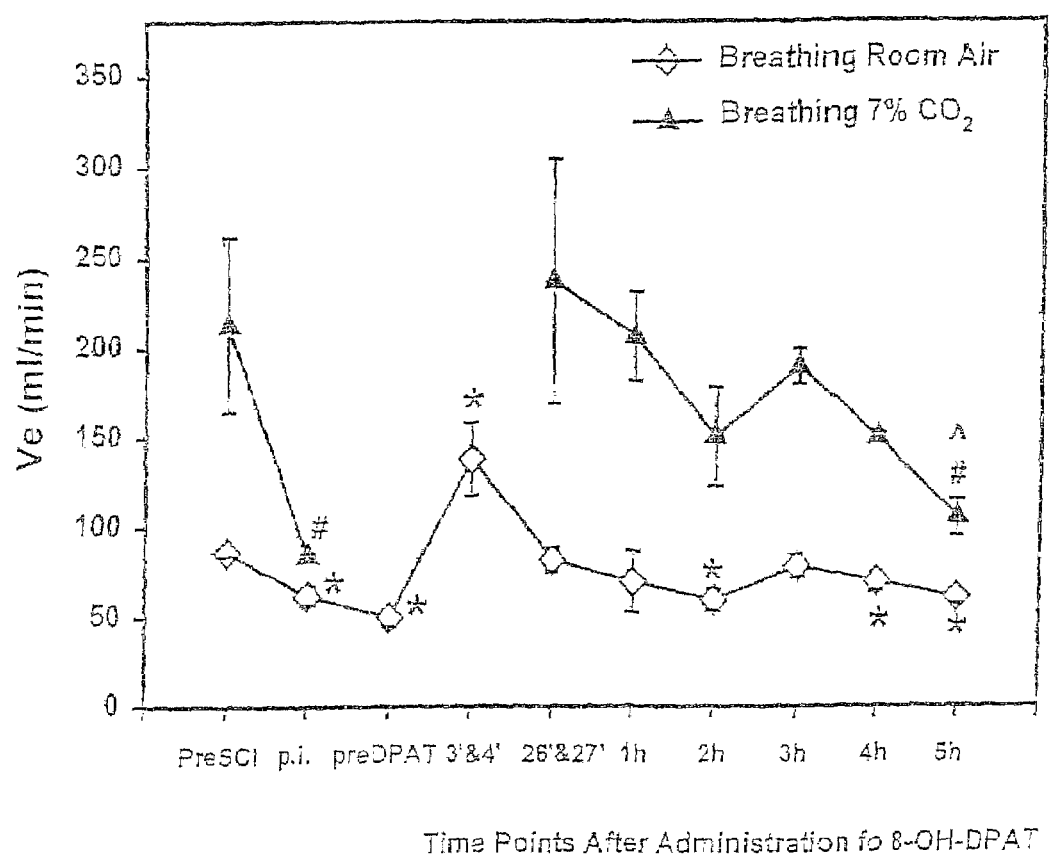
FIG. 3. Time-dependent effect of 8-OH-DPAT in minute ventilation in T8 rats at 24 hours post injury. Curves represent the average minute ventilation (Ve) for rats before SCI and after SCI (10 g×2.5 cm weight drop), and then prior to 8-OH-DPAT administration and after the drug injection (250 μg/kg in 0.5 ml/rat) at 24 hours post injury (p.i.; n=3). SCI resulted in a significant drop in baseline Ve (i.e. breathing room air), and the injury also significantly diminished Ve response to 7% CO2 challenge. 8-OH-DPAT treatment significantly improved baseline Ve at 4 minutes post drug injection (*$P<0.05$ compared to pre-injury baseline VE; #$P<0.05$ compared to pre-injury Ve under 7% $CO_2$ challenge; repeated measures ANOVA followed by Tukey's procedure). SCI rats (n=3) showed a time-dependent decline of their minute ventilation (Ve) in response to breathing 7% $CO_2$ (▲), or under room air breathing (◇) subsequent to a single dose of 8-OH-DPAT ($^\wedge$P<0.05 compared to Ve under 7% $CO_2$ challenge at 20 minutes after the administration of 8-OH-DPAT; one way ANOVA followed by Tukey's procedure). Note: the decline speed is much greater in the baseline conditions (i.e. breathing room air) than that under $CO_2$ challenge.

Considering the relative short systematic half life of 8-OH-DPAT in rats (T1/2:~50 minutes; Kleven and Koek, 1998), we decided to conduct a time-course study to determine if the respiratory effects of 8-OH-DPAT was time-related and thus, a dose-dependent event. At 24 hours p.i., the enhancing effect of 8-OH-DPAT on ventilatory response to 7% $CO_2$ challenge decreased in a time-dependent manner, with the values recorded at 5 hours after the drug injection being slightly and not significantly higher than those collected at 24 hours p.i. and before 8-OH-DPAT treatment (FIG. 3). Therefore, a single dose treatment of 8-OH-DPAT normalized ventilatory response to breathing 7% $CO_2$ for more than 2 hours after the drug administration (FIG. 3). Interestingly, although 8-OH-DPAT treatment also showed a time-dependent improvement of baseline Ve (i.e. under room air breathing), however, the effect was significant for only 1 hour (FIG. 3).

Example 3

Effects of 8-OH-DPAT on the Respiratory Function of Normal Rats

Normal rats without SCI demonstrated highly consistent respiratory parameters under baseline conditions and 7% $CO_2$ challenge relative to data collected at 24 hours pre-injury in the above SCI studies (compare Table 2 to Table 1) as well as to those reported earlier by our group (Teng et al., 1998a and 1999). Saline VEH injection (0.5 ml/per rat, i.p.) did not change respiratory parameters either in baseline conditions or under 7% $CO_2$ breathing compared to those obtained before VEH treatment (Table 2). In contrast, treatment of 8-OH-DPAT quickly and significantly enhanced respiratory function (Table 2). However, 8-OH-DPAT treatment only increased baseline Vt for 4 minutes in normal rats before it dropped back to previous levels (Table 2). On the other hand, the stimulating effect of 8-OH-DPAT on f lasted till the last minute of the observation (i.e. 23 minutes post drug administration) and with a strong potency (Table 2). This phenomenon of a stronger potency of 8-OH-DPAT on f than Vt obtained in normal animals was also noticed in SCI rats at 14, 21 and 28 days p.i. when the drug was given to chronic SCI rats with an already recovered respiratory function (data not shown). Strikingly, 8-OH-DPAT treatment in normal rats did not significantly alter ventilatory response to 7% $CO_2$ challenge starting at 24 minutes after the administration of 8-OH-DPAT (Table 2). This result brings up a sharp contrast between the effect of 8-OH-DPAT on $CO_2$-tringered ventilatory response in normal rats and animals with acute SCI (i.e. at 24 hours and 7 days p.i.; Table 1 and 2).

TABLE 2

Respiratory Parameters of Normal Conscious Rats That Received Systemic 8OH-DPAT

| Experimental Group | Prior to Treatments | | Post Saline (i.p.) | | Pre-8-OH-DPAT (250 μg/kg. i.p.) | 3 & 4 min post 8-OH-DPAT |
|---|---|---|---|---|---|---|
| | Baseline | 7% CO2 | Baseline | 7% CO2 | Baseline | Baseline |
| Normal Conscious Rats (n = 3) | Ti 0.23 ± 0.01 | 0.18 ± 0.02 | Ti 0.24 ± 0.03 | 0.17 ± 0.01 | Ti 0.24 ± 0.01 | Ti 0.19 ± 0.04 |
| | Te 0.54 ± 0.04 | 0.22 ± 0.04 | Te 0.51 ± 0.04 | 0.21 ± 0.02 | Te 0.69 ± 0.06 | Te 0.25 ± 0.09↓ |
| | Tv 0.89 ± 0.05 | 1.43 ± 0.04 | Tv 0.90 ± 0.09 | 1.37 ± 0.21 | Tv 1.04 ± 0.07 | Tv 1.14 ± 0.08↑ |
| | f 84.9 ± 7.58 | 169.9 ± 6.57 | f 87.2 ± 4.57 | 161.1 ± 10.2 | f 71.6 ± 6.02 | f 177.5 ± 36.2↑ |
| | Ve 75.1 ± 4.75 | 242.5 ± 44.5 | Ve 78.6 ± 6.97 | 224.5 ± 42.5 | Ve 74.0 ± 4.65 | Ve 198.6 ± 32.9↑ |

| Experimental Group | 11 & 12 min post 8-OH-DPAT Baseline | 21 & 22 min post 8-OH-DPAT Baseline | 7% CO2 at 31' & 32' after 8-OH-DPAT 7% CO2 |
|---|---|---|---|
| Normal Conscious Rats (n = 3) | Ti 0.16 ± 0.02 | Ti 0.18 ± 0.02 | Ti 0.19 ± 0.01 |
| | Te 0.30 ± 0.07↓ | Te 0.41 ± 0.08↓ | Te 0.23 ± 0.03 |
| | Tv 0.92 ± 0.05 | Tv 0.84 ± 0.02 | Tv 1.50 ± 0.14 |
| | f 149.8 ± 26.5↑ | f 134.4 ± 21.2↑ | f 155.6 ± 18.5 |
| | Ve 138.6 ± 27.6↑ | Ve 112.9 ± 15.2↑ | Ve 239.3 ± 48.9 |

↑ or ↓: Significantly higher or lower compared to pre-SCI values; $P < 0.05$, one way ANOVA followed by Tukey's or Dunn's test for multiple comparisons.

Example 4

Buspirone Treatment Improves Respiratory Function in Spinal-Cord Injured Rats

Figure 4:
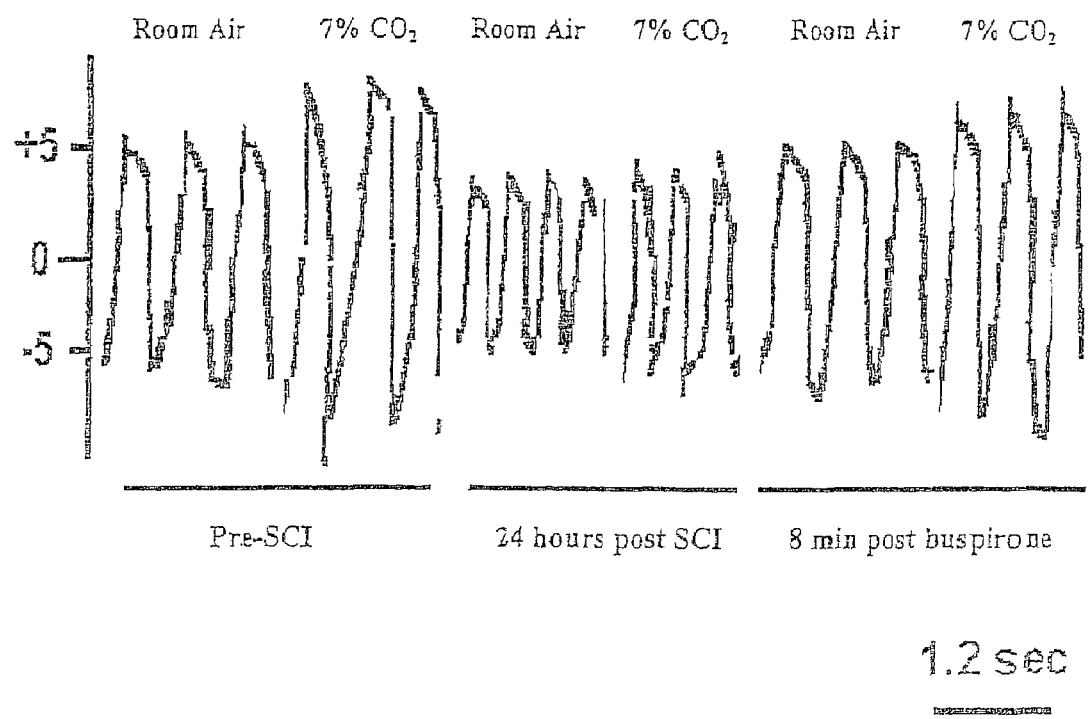
FIG. 4. Effect of buspirone treatment on respiratory function under baseline conditions or challenged by air mixtures of 7% $CO_2$ at 24 hours after SCI. Plethysmograph tracings of respiratory flow rate (unit: ml/sec) obtained from conscious rats breathing room air or an air mixture containing 7% $CO_2$ 24 hours prior to spinal cord injury and 24 hours p.i. Also given is respiratory flow rate tracing recorded before buspirone injection and after its administration when the animal was breathing room air or challenged by an air mixture containing 7% $CO_2$.

Treatment with buspirone, a partial agonist of $5HT_{1A}$ receptors (Hoyer and Schoeffter, 1991) also reversed the abnormal respiratory function resulting form T8 SCI at 24 hours p.i. SCI reduced Vt values (0.74±0.02 vs 1.09±0.04, Unit: ml; P<0.05, repeated measures ANOVA with Tukey's procedure) were incremented rapidly by buspirone treatment (1.5 mg/kg in 0.5 ml/per rat, i.p.) to levels indiscenible from pre-injury readings (FIG. 4 and Table 3). The effect of buspirone on Bt sustained up to 9 minutes after the drug administration. Unlike 8-OH-DPAT, the initial stimulating effect of buspirone on f was rather milder and more transient relative to that of 8-OH-DPAT (Table 1 and Table 3). Buspirone treatment restored f to normal range beginning at 6 minutes after the dosing (Table 3; some data not shown). In addition, treatment of buspirone normalized ventilatory response to 7% $CO_2$ challenge that was started at 9 minutes after buspirone administration (1.01±0.11 vs 1.09±0.04, unit: ml/min; P>0.05, repeated measures ANOVA with Tukey's procedure).

TABLE 3

Respiratory Parameters of Conscious SCI Rats That Received Buspirone at 24 Hours after SCI

| Experimental Group | Prior to T8 SCI | | 24 hours Post SCI | | Pre-buspirone (1.5 mg/kg, i.p.) |
|---|---|---|---|---|---|
| | Baseline | 7% CO2 | Baseline | 7% CO2 | Baseline |
| T8 SCI Rats That Received buspirone (1.5 mg/kg, i.p.) (n = 3) | Ti 0.18 ± 0.02 | 0.17 ± 0.01 | Ti 0.22 ± 0.01 | 0.17 ± 0.02 | Ti 0.23 ± 0.04 |
| | Te 0.40 ± 0.01 | 0.20 ± 0.01 | Te 0.21 ± 0.02↓ | 0.20 ± 0.02 | Te 0.23 ± 0.01↓ |
| | Tv 1.09 ± 0.04 | 1.62 ± 0.08 | Tv 0.74 ± 0.02↓ | 1.12 ± 0.11↓ | Tv 0.74 ± 0.04↓ |
| | f 104.4 ± 3.2 | 169.1 ± 7.7 | f 142.2 ± 9.6↑ | 168.5 ± 14.2 | f 134.7 ± 13.2↑ |
| | Ve 114.8 ± 5.7 | 274.0 ± 23.8 | Ve 105.8 ± 8.7 | 190.2 ± 29.8↓ | Ve 100.5 ± 14.7 |

| Experimental Group | 3 & 4 min post buspirone Baseline | 8 & 9 min post buspirone Baseline | 7% CO2 at 15 & 16 min after buspirone 7% CO2 |
|---|---|---|---|
| T8 SCI Rats That Received buspirone (1.5 mg/kg. i.p.) (n = 3) | Ti 0.19 ± 0.01 | Ti 0.20 ± 0.03 | Ti 0.17 ± 0.01 |
| | Te 0.27 ± 0.03↑ | Te 0.40 ± 0.05 | Te 0.21 ± 0.03 |
| | Tv 1.17 ± 0.13 | Tv 1.01 ± 0.11 | Tv 1.46 ± 0.14 |
| | f 143.5 ± 11.9↓ | f 101.2 ± 5.5 | f 162.6 ± 17.4 |
| | Ve 171.3 ± 30.1 | Ve 101.8 ± 11.4 | Ve 240.9 ± 44.8 |

↑ or ↓: Significantly higher or lower compared to pre-SCI values; $P < 0.05$, one way ANOVA followed by Tukey's or Dunn's test for multiple comparisons.

Example 5

Figure 5:
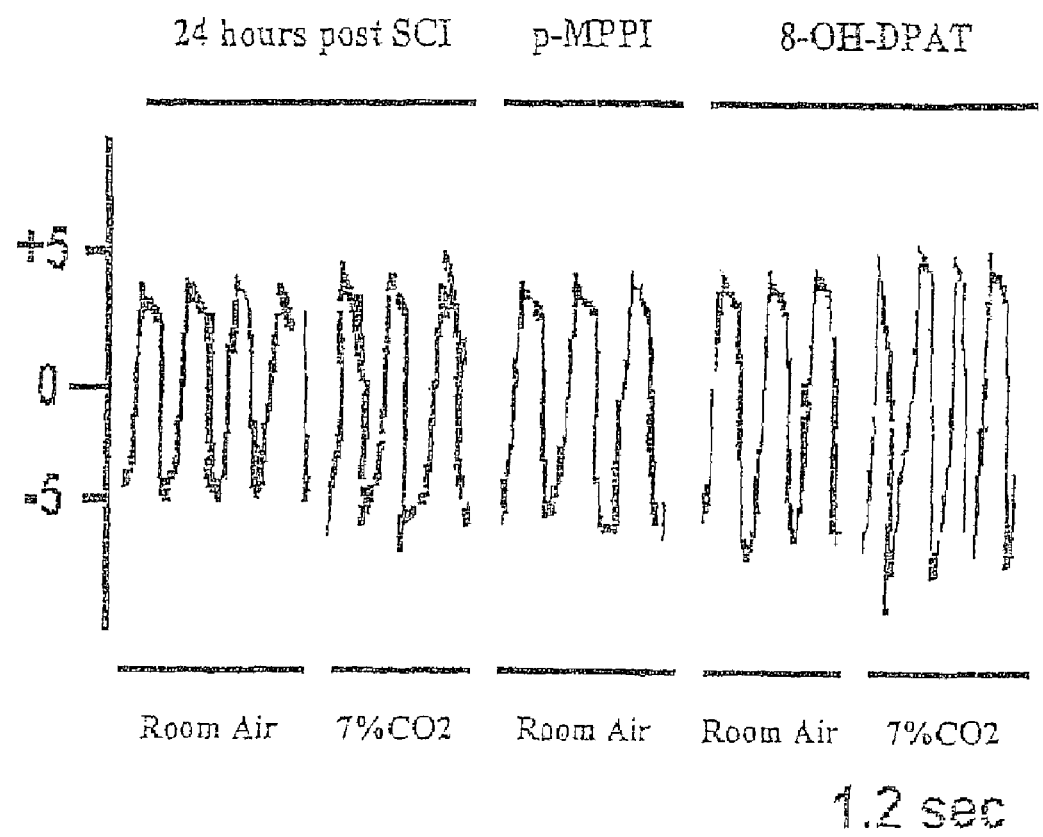
FIG. 5. Antagonistic effect of p-MPPI on 8-OH-DPAT-induced respiratory improvement unconscious rats at 24 hours after SCI. Plethysmograph tracings of respiratory flow rate (unit: ml/sec) obtained from conscious rats breathing room air or an air mixture containing 7% $CO_2$ 24 hours prior to spinal cord injury and 24 hours p.i. Also given is respiratory flow rate tracing recorded before buspirone injection and after drug administration.

The 5HT$_{1A}$-Receptor Anatagonist P-MPPI Specifically Reverses the 8-OH-DPAT-Mediated Improved of Respiratory Function in Spinal Cord Injured Rats Through testing whether a specific 5HT$_{1A}$-receptor antagonist, p-MPPI (Theilen et al., 1990) could efficiently block the stimulus effect of 8-OH-DPAT on respiratory function, we further studied the specificity of 8-OH-DPAT effects. The p-MPPI antagonism of 8-OH-DPAT was first studied by a series of dose titration experiments (data not shown). We found that a dose of 2 mg/kg (in 0.5 ml/per rat, i.p.) could substantially block the stimulating effects of 8-OH-DPAT on respiratory function. We also tested the effect of p-MPPI (3 mg/kg in 0.5 ml/rat, i.p.) per se on respiratory function in normal rats (n=3). No significant impacts of p-MPPI treatment were found on respiratory function of the normal rats, except that administration of p-MPPI resulted in a small but not significant increase in Vt, f and Ve (data not shown). Therefore, in the definitive study, this dose of p-MPPI (3 mg/kg in 0.5 ml/rat, i.p.) was given at 20 minutes before the administration of 8-OH-DPAT. Pre-treatment of p-MPPI significantly suppressed the effects of 8-OH-DPAT on respiration at 24 hours p.i. (FIG. 5). Pre-treatment of p-MPPI stabilized post-SCI baseline Vt, f and Ve at routine p.i. levels regardless of the later injection of 8-OH-DPAT (Table 4). In addition, the stimulating effects of 8-OH-DPAT on ventilatory response to 7% $CO_2$ at 24 hours p.i. were significantly blocked by treatment of p-MPPI (FIG. 5; Table 4).

animals exhibited a diminished response to the respiratory stimulating effect of 7% $CO_2$: minute ventilation (Ve) changed from 250.4±17.0 ml/min prior to SCI to 161.7±14.9 ml/min at 24 hours p.i. (P<0.05). Similar respiratory deficits were also observed in the SCI rats at 7 days p.i. (n=3). Treatment with the 5HT$_{1A}$ receptor agonist, 8-hydroxy-2-(di-n-propylamino)tetralin (8-OH-DPAT, 250 µg/kg; i.p.) at 24 hours or 7 days p.i. normalized Vt, f and the respiratory response to 7% $CO_2$. Results identical to those of 8-OH-DPAT were obtained with another 5HT$_{1A}$ receptor agonist, buspirone (1.5 mg/kg, i.p.; n=3). In contrast, saline vehicle administration (i.p.; n=5) showed no beneficial effects on SCI-impaired respiration. Finally, pretreatment with a specific antagonist of 5HT$_{1A}$ receptors, 4-(2'-methoxyphenyl)-1-[2'-[N-(2"-pyridinyl)-p-iodobenzamido]ethyl]piperazine (p-MPPI, 3 mg/kg, i.p.; n=3) given 20 min before 8-OH-DPAT administration, prevented 8-OH-DPAT from restoring respiration to normal. Our results demonstrate that drugs which stimulate 5HT$_{1A}$ receptors improve respiratory function in conscious rats after SCI.

Example 6

Buspirone Treatment Improves Respiratory Function in a Mutant Mouse Model of Familial ALS Based on the data presented above in Example 4 and the observation that both SCI-related and ALS-related respiratory abnormalities are triggered by muscle dysfunction (e.g., degeneration) which is mediated by denernvation, we determined whether buspirone treatment could ameliorate respi-

TABLE 4

Respiratory Parameters of Conscious SCI Rats That Pre-treated with p-MPPI before Administration of 8OH-DPAT

| Experimental Group | Prior to SCI | | 24 hours Post SCI | | 3 & 4 min post p-MPPI | 19 & 20 min post p-MPPI |
|---|---|---|---|---|---|---|
| | Baseline | 7% CO2 | Baseline | 7% CO2 | Baseline | Baseline |
| Normal Rats with Saline i.p. (n = 3) | Ti 0.27 ± 0.02<br>Te 0.52 ± 0.00<br>Tv 1.48 ± 0.02<br>f 78.5 ± 1.64<br>Ve 116.9 ± 2.4 | 0.22 ± 0.01<br>0.32 ± 0.06<br>2.37 ± 0.12<br>114.9 ± 13.9<br>269.4 ± 21.9 | Ti 0.26 ± 0.05<br>Te 0.35 ± 0.01↓<br>Tv 0.66 ± 0.04↓<br>f 101.8 ± 7.2<br>Ve 67.4 ± 8.7↓ | 0.22 ± 0.02<br>0.30 ± 0.01<br>0.84 ± 0.03<br>118.8 ± 3.8<br>99.9 ± 6.1 | Ti 0.33 ± 0.01<br>Te 0.28 ± 0.02↓<br>Tv 0.75 ± 0.08↓<br>f 103.2 ± 5.4↑<br>Ve 76.9 ± 4.6↓ | Ti 0.28 ± 0.04<br>Te 0.54 ± 0.10<br>Tv 0.77 ± 0.08↓<br>f 76.2 ± 7.7<br>Ve 57.8 ± 4.1↓ |

| Experimental Group | 3 & 4 min post 8-OH-DPAT Baseline | 9 & 10 min post 8-OH-DPAT Baseline | 7% CO2 at 16' & 17' after 8-OH-DPAT 7% CO2 |
|---|---|---|---|
| Normal Rats with Saline i.p. (n = 3) | Ti 0.32 ± 0.02<br>Te 0.32 ± 0.08↓<br>Tv 0.85 ± 0.14↓<br>f 99.4 ± 9.1↑<br>Ve 82.5 ± 10.9↓ | Ti 0.31 ± 0.02<br>Te 0.28 ± 0.02↓<br>Tv 0.82 ± 0.11↓<br>f 107.5 ± 1.9↑<br>Ve 88.3 ± 13.3↓ | Ti 0.19 ± 0.02<br>Te 0.32 ± 0.05<br>Tv 1.15 ± 0.21↓<br>f 126.8 ± 14.4<br>Ve 143.1 ± 28.1↓ |

↑or ↓: Significantly higher or lower compared to pre-SCI values; P < 0.05, one way ANOVA followed by Tukey's or Dunn's test for multiple comparisons.
Note: This is the only group of rats with body weight that ranged between 360 and 390 grams. Thus, the higher pre-SCI Vt values and lower f were due to body size as previously described (Teng et al., 1999).

SUMMARY

T8 SCI rats (n=5) showed decreased tidal volume (Vt: 0.9±0.02 to 0.66±0.03 ml: P<0.05) and increased respiratory rate (f, 90.8±3.7 to 131.6±5.7; P<0.05) under room air ventilation at 24 hours post injury (p.i.). Moreover, these ratory abnormalities (e.g., deficits in tidal volume and respiratory rates) in SOD1 mice. SOD1 mice are mutant mice which provide an animal model for an inherited form of ALS which is more commonly referred to as familial ALS. Respiratory function was determined prior to (e.g., pre) and after (e.g., post) buspirone administration. Baseline tidal volumes and respiratory rates were determined prior to the intraperitoneal or subcutaneous administration of buspirone at a dose of 3.0 mg/kg. These parameters of respiratory function were subsequently reevaluated 2 minutes after drug treatment. The data presented in FIGS. 6 and 7 demonstrate that the subcutaneous administration of buspirone significantly improved the respiratory function (e.g., increased tidal volume and decreased respiratory rate) of the treated mice.

These results are consistent with the theory that 5HT 1A agonists can be used to counteract (e.g., ameliorate) the respiratory abnormalities mediated by ALS pathophysiology. While not wishing to be bound by theory, it is believed that 5HT 1A agonists improve respiratory function by stimulating respiratory premotoneurons in the brain stem and spinal cord. Consistent with this theory, it is further hypothesized that the proper stimulation of motoneurons, for example by the administration of of a 5HT 1A agonist such as buspirone, could delay the muscular degeneration (e.g., dystrophy and atrophy) associated with the pathophysiological consequences of ALS. It si also hypothesized that the coadministration of a β2-adrenergic agonist in combination with a 5HT 1A agonist could mediate a synergistic effect which will further inhibit ALS-related muscular degeneration. The predicted synergism is predicated on the ability of β2-adrenergic agonists to promote muscle hypertrophy and to increase the expression of neural growth (e.g. NGF and bFGF) and trophic factors. Thus, a treatment strategy comprising the coadministration of a 5HT 1A agonist (e.g., 8-OH-DPAT or buspirone) in combination with a β2-adrenergic agonist (e.g., clenbuterol or salbutanol) provides a novel therapeutic strategy for the treatment of ALS.

REFERENCES CITED IN DETAILED DESCRIPTION

The following references have been cited in the detailed description of the instant invention. The relevant teachings of all references cited herein are hereby incorporated by reference.

Al-Zubaidy Z A, Erickson R L, Greer J J (1996) Serotonergic and noradrenergic effects on respiratory neural discharge in the medullary slice preparation of neonatal rats. Plfugers Arch—Eur J Phusiol 431:942–949.

Bach K B, Mitchell G S (1996) Hypoxia-induced long-term facilitation of respiratory activity is serotonin dependent. Respir Physiol 104:251–260.

Baker H J, Lindsey J R, Weisbroth S H (1979) The laboratory rat, biology and diseases. pp 411–412. Orlando: Academic Press, Inc.

Basso D M, Beattie M S, Bresnahan J C (1995) A sensitive and reliable locomotor rating scale for open field testing in rats. J Neurotrauma 12:1–21.

Crowe M J, Bresnahan J C, Shuman S L, Masters J N, Beattie M S (1997) Apoptosis and delayed degeneration after spinal cord injury in rats and monkeys. Nat Med 3:73–76.

Dorato, M A, Carlson, K H and Copple, D L (1983) Pulmonary mechanics in conscious Fischer 344 rats: multiple evaluations using nonsurgical techniques. Toxicol Appl Pharmacol 68:344–353.

Feldman, J L, McCrimmon, D R (1999) Neural control of breathing. In: Zigmond, M F, Bloom, F E, Landis, S C, Roberts, J L, Squire, L R (eds), Fundamental Neuroscience. Pp 1063–1090. San Diego: Academic Press.

Ferreira, M. Sahibzada N, Wassennan A M, Taveira-DaSilva A M, Dretchen, K L, Gillis R A (1998) Reversal of morphine-induced apnea by 5-HT1A receptors (abstract). FASAB 12:A495.

Fozard J R, Mir A K, Middlemiss D N (1987) Cardiovascular response to 8-hydroxy-2-(di-n-propylamino)tetralin (8-OH-DPAT) in the rat: site of action and pharmacological analysis. J Cardiovas Pharmacol 9:329–347.

Frankel, H L, Coll, Jr, Charlifue, S W, Whitenect, G G, Gardner, B P, Jamous, M A, Krishnan, K R, Nuseibeh, I, Savic, G, Sett, P (1998) Long-term survival in spinal cord injury: a fifty year investigation. Spinal Cord 36:266–274.

Gale, K, Kerasidis H, Wrathall J R (1985) Spinal cord contusion in the rat: behavioral analysis of functional neurological impairment. Exp Neurol 88:123–134.

Gibson, J G, Pride, N B, Newsom Davis, J, Loh, L C (1977) Pulmonary mechanics in patients with respiratory muscle weakness. Am Rev Respir Dis 115:389–395.

Holstege, G (1991) Descending motor pathways and the spinal motor system: Limbic and nonlimbic components. Pro Brain Res 97:307–421.

Hamon M, Cossery J M, Spampinato U, Gozlan H (1986) Are there selective ligand for $5HT_{1A}$ and $5HT_{1B}$ receptor binding sites in brain? TIPS 346:336–338. Hoyer D, Schoeffter P (1991) 5HT receptors: Subtype and second messengers. J Receptor Res 11: 197–214.

Jackson D A, White S R (1990) Receptor subtypes mediating facilitation by serotonin of excitability of spinal motoneurons. Neuropharmacol 29: 787–797.

Kinkead R, Zhan W Z, Prakash Y S, Bach K B, Sieck G C, Mitchell G S (1998) Cervical dorsal rhizotomy enhances serotonergic enervation of phrenic motoneurons and serotonin-dependent long-term facilitation of respiratory motor output in rats. J Neurosci 18:8436–8443.

Kleven, M S, Koek, W (1998) Discriminative stimulus effects of 8-hydroxy-2-(di-n-propylamino)tetralin in pigeons and rats: species similarities and differences. J Pharmacol Exp Ther 284:238–243.

Lalley P M (1994) The excitability and rhythm of medullary respiratory neurons are attenuated by the serotonin receptor agonist 5-methoxy-N,N-dimehtyltryptamine. Brain Res 648:87–98.

Lalley P M, Bischoff, A M, Richter D W (1994) Serotonin 1A receptor activation suppresses respiratory apneusis in the cat. Neurosci Lett 172:59–62.

Liu, X Z, Xu, X M, Hu, R, Du, C, Zhang, S X, McDonald, J W, Dong, H X, Wu, Y J, Fan, G S, Jacquin, M F, Hsu, C Y, Choi, D W (1997) Neuronal and glial apoptosis after traumatic spinal cord injury. J Neurosci 15:5395–5406.

Mansel, J K, Norman, J R (1990) Respiratory complications and management of spinal cord injuries. Chest 97:1446–1452.

Middlemiss D, Fozard J R (1983) 8-Hydroxy-2-(dipropylamino)-tetralin discriminates between subtypes of the 5HT recognition site. Eur J Pharmac 90:151–153.

Noble L J, Wrathall J R (1985) Spinal cord contusion in the rat: morphometric analyses of alterations in the spinal cord. Exp Neurol 88:135–149.

Noble L J, Wrathall J R (1989) Correlative analysis of lesion development and functional status after graded spinal cord contusive injuries in the rat. Exp Neurol 103:34–40.

Onimaru H, Shamoto A, Homma I (1998) Modulation of respiratory rhythm by 5HT in the brainstem-spinal cord preparation from new born rat. Pflugers Arch-Eur J Physiol 435:485–494.

Prakash, U B S (1989) Neurologic diseases. In: Textbook of Pulmonary Diseases (Baum, G L, Wolinsky E eds), $4^{th}$ Ed, Vol 2, pp 1409–1436. Boston: Little, Brown.

Slaok, R S and Shuoart, W (1994) Respiratory dysfunction associated with traumatic injury to the central nervous system. Clin Chest med 15:739–749.

Smith J C, Ellenberger H H, Ballanye K, Richter D W, Feldman J L (1991) Pre-Botzinger complex: a brainstem region that may generate respiratory rhythm in mammals. Science 254:726–729.

Teng, Y D, Mocchetti, I, Taveira-DaSilva, A M, Gillis, R A, Wrathall, J R (1998a) Basic and acidic fibroblast growth factor (FGF2) improves respiratory function after contusive spinal cord injury—a dose-response study (abstract). J Neurotrauma 15: 899.

Teng, Y D, Mocchetti, I, Taveira-DaSilva, A M, Gillis, R A, Wrathall, J R (1999) Basic fibroblast growth factor increases long-term survival of spinal motor neurons and improves respiratory function after experimental spinal cord injury. J Neurosci in press.

Teng, Y D, Mocchetti, I, Wrathall, J R (1998b) Basic and acidic fibroblast growth factors protect spinal motor neurons in vivo after experimental spinal cord injury. Eur J Neurosci 10:798–802.

Teng, Y D, Wrathall, J R (1997) Local blockade of sodium channels by tetrodotoxin ameliorates tissue loss and long-term functional deficits resulting from experimental spinal cord injury. J Neurosci 17:4359–4366.

Thielen R J, Fangon N B, Frazer A (1996) 4-(2'-methoxyphenyl)-1-[2'-[N-(2"-pyridinyl)-p-iodobenzamido]ethyl]piperazine and 4-(2'-methoxyphenyl)-1-[2'-[N-(2"-pyridinyl)-p-fluorobenzamido]ethyl]piperazine, two new antagonists at pre- and postsynaptic serotonon-1A receptors. J Pharmocal Exp Ther 277:661–670.

Troyer, A D, Heilpom, A (1980) Respiratory mechanics in quadriplegia. The respiratory function of the intercostal muscle. Am Rev Respir Dis 122:591–600.

Wilken B, Lalley P, Bischoff A M, Christien H J, Behnke J, Hanefeld F and Richter D W (1997) Treatement of apneustic respiratory desturbance with a serotonin-receptor agonist. J Pediatr 130:89–94.

Wrathall J R, Choiniere D, Teng Y D (1994) Dose-dependent reduction of tissue loss and functional impairment after spinal cord trauma with the AMPA/kainate antagonist NBQX. J Neurosci 14:6598–6607.

Wrathall, J R, Pettegrew, R, Harvery, F (1985) Spinal cord contusion in the rat: production of graded, reproducible injury groups. Exp Neurol 88:108–122.

Agbenyega E. T. et al. Effect of clenbuterol on normal and denervated muscle growth and contractility. Muscle Nerve 13:199–203, 1990.

Bardsley, R. G. et al. Effect of β-agonists on expression of calpain and calpastatin activity in skeletal muscle. Biochimie 74:267–273, 1992.

Culmsee, C. et al. Clenbuterol induces growth factor mRNA, activates astrocytes, and protects rat brain tissue against ischemic damage. Eur. J. Pharmacol. 379:33–45, 1999 (a).

Zeman, R. J. et al. Clenbuterol, a β2-agonist, retards atrophy in denervated muscles. Am. J. Physiol. 252 (Endocrinol. Metab. 15): E152–E155, 1987.

Zeman, R. J. et al. Slow to fast alterations in skeletal muscle fibers caused by clenbuterol, a β2-receptor agonist. Am. J. Physiol. 254:E726–E732, 1988.

Zeman, R. J. et al. Clenbuterol, a β2-receptor agonist, retards wasting and loss of contractility in irradiated dystrophic mdx muscle. Am. J. Physiol. 267:C865–C868, 1994.

Zeman, R. J. et al. Clenbuterol, a beta (2)-adrenoceptor agonist, improves locomoter and histological outcomes after spinal cord contusion in rats. Exp. Neurol. 159:267–273, 1999.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of improving respiratory function in an individual with abnormal respiratory function resulting from spinal cord respiratory motor neuron injury or degeneration comprising administering an agent selected from the group consisting of: a serotonin (5HT) receptor type 1A agonist and a β2-adrenergic agonist, wherein the β2-adrenergic agonist is selected from the group consisting of clenbuterol and salbutamol and wherein the serotonin (5HT) receptor type 1A agonist is selected from the group consisting of 8-OH-DPAT and buspirone.

2. The method of claim 1 wherein the individual with abnormal respiratory function is afflicted with ALS.

3. The method of claim 1 wherein the individual with abnormal respiratory function suffers from a signal cord injury.

4. A method of treating an individual with ALS induced respiratory abnormalities to restore respiratory function comprising administering a serotonin (5HT) receptor type 1A agonist a combination with a β2-adrenergic agonist, wherein the serotonin (5HT) receptor type 1A agonist is selected from the group consisting of 8-OH-DPAT and buspirone an wherein the β2-adrenergic agonist is selected from the group consisting of clenbuterol and salbutamol.

5. The method of claim 4 wherein the serotonin (5HT) receptor type 1A agonist in combination with a β2-adrenergic agonist restores the respiratory abnormalities of decreased tidal volume and increased respiratory rate to normal.

6. A method of improving respiratory abnormalities in an individual afflicted with ALS induced respiratory abnormalities comprising administering a serotonin (5HT) receptor type 1A agonist in combination with a β2-adrenergic agonist, wherein the serotonin (5HT) receptor type 1A agonist is selected from the group consisting of 8-OH-DPAT and buspirone and wherein the β2-adrenergic agonist is selected front the group consisting of clenbuterol and salbutamol.

7. The method of claim 6 wherein the serotonin (5HT) receptor type 1A agonist in combination with a β2-adrenergic agonist restores the ALS induced respiratory abnormalities of decreased tidal volume and increased respiratory rate to normal.

8. A method of treating an individual with spinal cord injury induced respiratory abnormalities by administering a serotonin (5HT) receptor type 1A agonist, wherein the serotonin (5HT) receptor type 1A agonist is selected from the group consisting of 8-OH-DPAT and buspirone.

9. The method of claim 8 wherein the serotonin (5HT) receptor type 1A agonist restores the respiratory abnormalities of decreased tidal volume and increased respiratory rate to normal.

10. A method of treating an individual with ALS induced respiratory abnormalities comprising administering a serotonin (5HT) receptor type 1A agonist, wherein the serotonin (5HT) receptor type 1A agonist is selected from the group consisting of 8-OH-DPAT and buspirone.

11. The method of claim 10 wherein the serotonin (5HT) receptor type 1A agonist restores the respiratory abnormalities of decreased tidal volume and increased respiratory rate to normal.

* * * * *

UNITED STATES PATENT AND TRADEMARK OFFICE
CERTIFICATE OF CORRECTION

| | | |
|---|---|---|
| PATENT NO. | : 7,071,194 B2 | Page 1 of 1 |
| APPLICATION NO. | : 10/244087 | |
| DATED | : July 4, 2006 | |
| INVENTOR(S) | : Yang D. Teng | |

It is certified that error appears in the above-identified patent and that said Letters Patent is hereby corrected as shown below:

<u>Column 22,</u>

Line 20, delete "signal" and insert -- spinal --

Signed and Sealed this

Nineteenth Day of September, 2006

JON W. DUDAS
*Director of the United States Patent and Trademark Office*